(12) United States Patent
Förster

(10) Patent No.: US 8,167,613 B2
(45) Date of Patent: May 1, 2012

(54) SCREW-TYPE IMPLANT, PARTICULARLY FOR ORTHODONTICS

(75) Inventor: Rolf Förster, Pforzheim (DE)

(73) Assignee: Bernhard Förster GmbH, Pforzheim (DE)

( * ) Notice: Subject to any disclaimer, the term of this patent is extended or adjusted under 35 U.S.C. 154(b) by 568 days.

(21) Appl. No.: 12/069,692

(22) Filed: Feb. 12, 2008

(65) Prior Publication Data

US 2008/0193898 A1    Aug. 14, 2008

(30) Foreign Application Priority Data

Feb. 14, 2007  (DE) .......................... 10 2007 007 289
Apr. 11, 2007  (DE) .......................... 10 2007 017 137

(51) Int. Cl.
*A61C 3/00* (2006.01)

(52) U.S. Cl. .......................... 433/18; 433/174

(58) Field of Classification Search .......... 433/172–175, 433/199.1, 201.1, 2, 5–24; 606/65–66; 623/16.11, 623/17.17; 411/411–412, 417–418, 451.1
See application file for complete search history.

(56) References Cited

U.S. PATENT DOCUMENTS

| | | | | |
|---|---|---|---|---|
| 994,330 A * | 6/1911 | Morris | .......................... | 411/453 |
| 2,263,137 A * | 11/1941 | Oestereicher | .................. | 411/413 |
| 3,176,746 A * | 4/1965 | Walton | .......................... | 411/259 |
| 3,726,330 A * | 4/1973 | Adler | ............................ | 411/168 |
| 3,856,065 A * | 12/1974 | Gehring | ........................ | 411/302 |
| 4,024,899 A * | 5/1977 | Stewart | ........................ | 411/277 |
| 4,329,099 A * | 5/1982 | Shimizu et al. | ............... | 411/412 |
| 4,474,556 A * | 10/1984 | Ellis et al. | ...................... | 433/173 |
| 4,874,278 A * | 10/1989 | Kawashita | ..................... | 411/386 |
| 5,871,356 A * | 2/1999 | Guedj | ............................ | 433/174 |
| 5,906,616 A * | 5/1999 | Pavlov et al. | .................. | 606/247 |
| 6,056,491 A * | 5/2000 | Hsu | ................................ | 411/418 |
| 6,102,703 A * | 8/2000 | Day | ............................... | 433/174 |
| 6,273,722 B1 * | 8/2001 | Phillips | ......................... | 433/174 |
| 6,328,516 B1 * | 12/2001 | Hettich | ........................ | 411/387.2 |
| 6,336,779 B1 * | 1/2002 | Jakob et al. | ................... | 411/175 |
| 6,789,991 B2 * | 9/2004 | Hsu | ................................ | 411/387.6 |
| 7,214,020 B2 * | 5/2007 | Suzuki | .......................... | 411/417 |
| 2003/0007845 A1 * | 1/2003 | Gens | ............................. | 411/411 |
| 2003/0069582 A1 | 4/2003 | Culbert | | |
| 2004/0267265 A1 | 12/2004 | Kyle | | |
| 2005/0069396 A1 * | 3/2005 | Wu | ................................ | 411/411 |
| 2006/0223030 A1 | 10/2006 | Dinkelacker | | |

FOREIGN PATENT DOCUMENTS

| | | |
|---|---|---|
| DE | 43 32 075 A1 | 3/1994 |
| DE | 697 09 464 T2 | 10/2002 |
| EP | 0 790 038 A1 | 8/1997 |
| EP | 1 709 937 A1 | 10/2006 |
| WO | WO 2004/060196 A1 | 7/2004 |

OTHER PUBLICATIONS

"Aarhus Mini Implant" manufactures web-page http://www.medicon.de/jsp/article_image.jsp?id=8785&art=12352&languageId=1&sh....

\* cited by examiner

*Primary Examiner* — Cris L Rodriguez
*Assistant Examiner* — Hao D Mai

(57) ABSTRACT

The description relates to a self-drilling threaded screw implant, particularly for orthodontics. According to the invention there is in at least one thread groove (15) of the thread (10), delimited by two flanks (13), a cutting edge (16) extending transversely to the two flanks (13) without traversing the two flanks (13).

18 Claims, 1 Drawing Sheet

SCREW-TYPE IMPLANT, PARTICULARLY FOR ORTHODONTICS

The invention relates to a screw implant with a self-drilling thread that is particularly appropriate for orthodontics.

Self-drilling anchor screws labeled "Aarhus Mini Implant" which are screwed through the gums into the jaw are offered by Medickon eG in D-75832 Tuttlingen, Germany. These screws have a head with a cross-shaped slot at which an apparatus for teeth alignment correction can be anchored. Such anchor screws remain only temporarily in the jaw, e.g., for the duration of the orthodontic treatment. They are provided with a drill tip and a self-drilling thread so that they can be screwed into the jaw without the need of a predrilling of the jaw.

The tip of the known anchor screw has a cutting edge formed by milling, which allows an easier insertion of the tip into the jawbone. Because of the milling, however, the tip is very weak and its durability and loading capacity leave much to be desired. The thread bordering the tip cuts into the jawbone, dislodging bone material which can be painful because concomitantly a considerable resistance has to be overcome.

DE 43 32 075 B4, WO 2004/060196 A1 and EP 1 709 937 A1 disclose screw implants for orthodontic purposes that are not self-drilling but rather require predrilling of the jawbone. For easier entry into the jawbone they are provided with routings extending either in a paraxial (EP 1 709 937 A1, DE 43 32 075 B4) or curved (WO 2004/060196 A1) manner which, starting from the tip of the screw implant, extend through several turns. These routings form cutting edges by means of which bone material is cut away during the screwing-in of the screw implants. After the screwing-in of the screw implant into the jawbone, bone tissue grows into the routings improving the hold of the screw implant in the jawbone. The screw implants of such type are not suitable for an only temporary insertion into the jawbone because they are rather difficult to remove.

SUMMARY OF THE INVENTION

The object of the present invention is to create a screw implant particularly suitable for orthodontics, which can be easily screwed-in and removed from the jawbone and is particularly appropriate as a temporary anchor screw for orthodontic treatment.

This object is attained by a screw implant with the features set forth in claim 1. Other advantageous embodiments of the invention are the object of the dependent claims.

The screw implant according to the invention is provided with a self-drilling thread which has in one or several turns a cutting edge extending transversely to the two flanks that delimit the thread groove in each of the turns. The cutting edge does not traverse the two flanks. Thus, the cutting edge is in the thread groove and can extend up to the two flanks delimiting the thread groove without, however, traversing it so that the external screw-shaped or helical edge of the thread radially adjacent to the flanks is not broken by the cutting edge traversing the thread groove.

This has several advantages:

With the aid of at least one cutting edge, but preferably several ones, each arranged transversely to the thread in a thread groove, it is easier to screw-in the screw implant into the bone.

The screwing-in of the screw implant is less painful for the patient.

Because of the additional cutting edges, not as much bone material is dislodged when screwing-in the screw implant into the bone but, rather, a part of the bone material is cut away by the at least one additional cutting edge and moved deeper into the bone.

As the screw-like or spiral-like outer edge of the thread is uninterrupted, it imparts a better hold in the bone than screw implants with routings extending from the beginning over several turns. The better hold can be achieved without the conic core disclosed in EP 1 709 937 A1 and WO 2004/060196 A1.

The screw implant according to the invention is resilient can from the beginning.

The screw implant according to the invention can be easily removed. Bone material that has grown into the recesses, provided in the grooves of the thread to form the cutting edges, does not impair the screwing out of the screw implant because it is in the "shadow area" of the cutting edge and, therefore it is not cut but only dislodged when the screw implant is screwed-out. In contrast to screw implants in which milled-out portions can extend uninterrupted over several turns, bone tissue cannot grow into the gaps of the flanks because a screw implant according to the invention has no such gaps.

A milled-out recess at the tip of the screw implant is not necessary so that it can bear a greater load than known anchor screws.

The simplest way of forming the cutting edge is to provide a recess in a turn of the thread groove between two opposite flanks of the thread, the cutting edge being an edge of that recess. Preferably, the recess extends into the core of the screw implant, i.e., that in comparison with an ordinary screw implant part of the core material in the thread groove is removed. Whether the recess is exclusively in the core of the screw implant or also extends into the flanks of the thread depends on the chosen type of thread. In the case of a thread with a trapezoidal thread groove profile, the forming of the cutting edge may be limited to the core. In the case of a curved flank profile, the recess may also extend into the flank. In particular, if the profile of the thread is formed mainly or continuously in curved manner, the recess, which is limited by the cutting edge, may extend into the flank of the profile. However, the cutting edge should not transverse the flanks; the screw-shaped or, respectively, helical outer edge of the thread is not be interrupted. Preferably, the cutting edge, measured from its deepest point in a radial direction, extends over not more than 70% of the depth of a thread groove. In this way the screw-shaped or helical outer edge, respectively, retains sufficient mechanical stability for the screwing-in process and for the anchoring in the bone even in the area of the recess limited by the cutting edge extending transversely to the flanks. Especially in the case of thread grooves having a cross-section with an asymmetric profile, the cutting edge can extend into one of the flanks of the thread groove in a radial direction farther outwards than into the other flank of the same thread groove.

The additional cutting edge can be configured in various ways. Preferably, it is on a plane on which—depending on the chosen profile of the thread—it can have a different course. The plane comprising the cutting edge is preferably parallel to the longitudinal axis of the screw implant; especially preferred is that it comprises the longitudinal axis of the screw implant. That is especially favorable for the screwing-in process. The plane comprising the cutting edge can also transverse the longitudinal axis of the screw implant at an angle. This angle, however, shall not be greater than ±15°, preferably not greater than ±10°.

The profile of the thread can be configured in various ways. A self-grooving profile of the thread is preferred. However, a self-cutting thread is also suitable. Compared with a self-cutting thread, a self-grooving thread has the advantage that, from the very first beginning, the screw implant sits stronger in the bone and, from the beginning, is fully resilient without first having to grow-in.

The screw implant, according to the invention, has at least one cutting edge that extends transversal to the flanks of the thread in a thread groove. Preferably, it has several of such cutting edges that are, preferably, distributed over the entire length of the thread. Should the cutting edges not be distributed over the entire length of the thread, they should preferably be in a section adjoining the tip of the thread because there they would be most effective.

For the manufacture of the screw implant it would be simplest if all the cutting edges would be on a common plane. However, for a practical application it is better if they are arranged around the core of the screw implant, especially in a regular disposition.

The recess provided in each turn in the thread groove to provide the cutting edge is preferably delimited by a part of the cylindrical barrel surface, whose axis runs transversely to the longitudinal axis of the screw implant and at a distance of same. The simplest manner to produce such a recess is by milling, whereby the screw implant is clamped and a micro milling-cutter is successively moved transversely in those thread grooves in which the cutting edges are to be formed. The milling tool is preferably positioned in such a manner that the recess ends flush at a radial plane of the screw implant at which the cutting edge is forming an edge of the recess.

The invention is especially suitable for screw implants whose core diameter is the same in all or almost all thread grooves, i.e. turns, with the exception of grooves close to a tapering tip. A conic core which in the case of other screw implants might be required on grounds of a firm seating is not required, but possible for screw implants according to the invention. For the configuration and application of the screw implant, according to the invention, as a temporary anchor screw for orthodontic treatments it can be advantageous to choose the core diameter in the last turn before the head of a anchor screw somewhat greater, or the pitch of the thread in the area of the backmost turn or turns somewhat less than in the area of the front thread turns. Thereby a particularly good firm seating is attained at the head of the anchor screw which is reinforced by an increased compression of the bone. During orthodontic treatment forces act on the head of the screw implant.

Between the head and the thread of the anchor screw may advantageously be a cylindrical and/or conic thread-free shank that is particularly well compatible with the gums surrounding the shank during orthodontic treatment.

BRIEF DESCRIPTION OF THE DRAWINGS

An embodiment of the invention is illustrated in the accompanying drawings, wherein.

DETAILED DESCRIPTION

Figure 1:
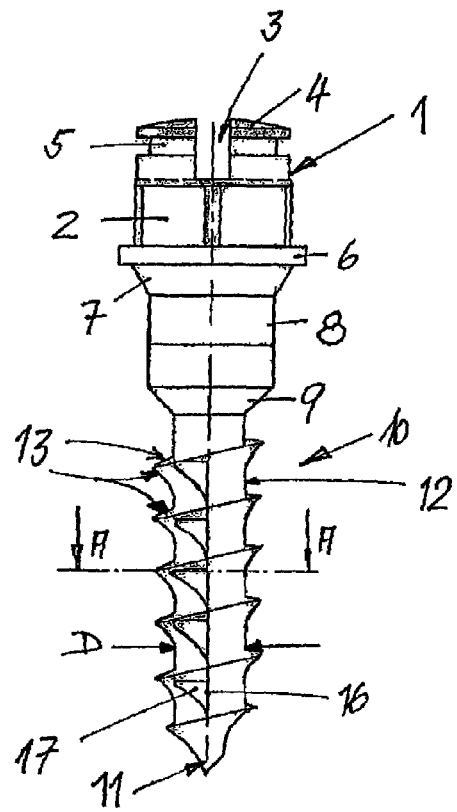
FIG. 1 shows a lateral view of a greatly enlarged orthodontic anchor screw

The anchor screw 1 has a head 1 with an outer octagon 2 for the gripping of a wrench. Other configurations that allow a torque transmission by means of a positive locking are also possible such as, e.g., an hexagon, generally a polygon head. The head 1 is provided with a cross-shaped slot 3 that is opened by boring beneath a cap 4 traversed by the cross-shaped slot 3. Underneath the cap 4, the head 1 is provided with an external annular groove 5. By virtue of the annular groove 5 and the cross-shaped slot 3 an orthopedic apparatus can be anchored by a wire at the head of the anchor screw.

A collar 6 is attached to the outer octagon 2 that serves as a limit stop for the wrench. A smooth conic section 7 follows the collar 6, which section changes to a smooth cylindrical shank 8. Anther conic section 9 follows the shank 8 that becomes a threaded part 10 which ends in a tip 11.

Figure 2:
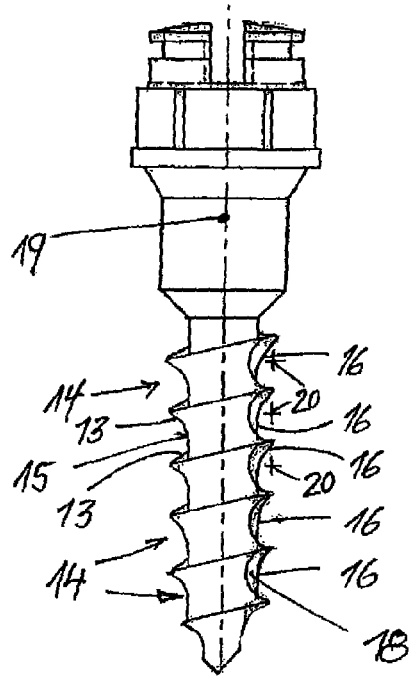
FIG. 2 shows the same anchor screw as in FIG. 1 in a lateral view turned 90° with respect to it
Figure 3:
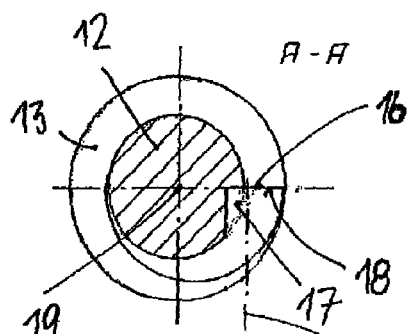
FIG. 3 shows the cross-section A-A through the anchor screw according to FIG. 1.
Figure 4:
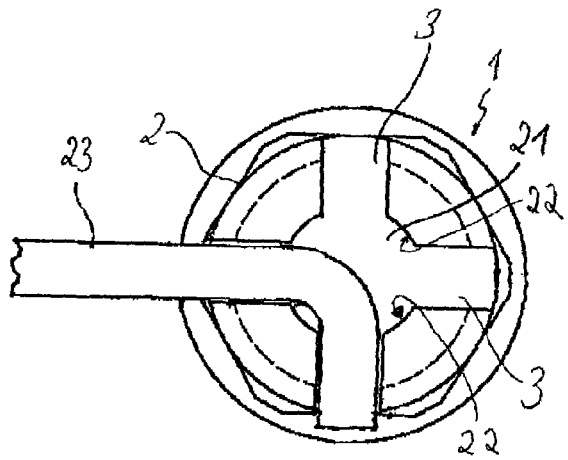
FIG. 4 shows a top view of the head of the anchor screw according to FIG. 1.

With exception of its tip 11, the threaded part 10 has a constant core diameter D along its entire length. Around the core 12 winds a single-flight, self-grooving thread, whose flanks 13 or thread grooves 15, respectively, have an asymmetrical profile. The core 12 is solid as evidenced by the solid cross latching shown in FIG. 3. Alternatively, a multiple thread can also be used. In each turn 14 after the point 11 the groove 15 has between each two flanks 13 a cutting edge 16. The cutting edge 16 is on a radial plane containing the longitudinal axis 19 of the anchor screw and which in FIG. 1 is vertical to the drawing plane while in the illustration of FIG. 2 it coincides with the drawing plane. The cutting edge 16 is an edge of a recess that is delimited by an area 17 that is part of a cylinder barrel surface, the axis 20 of which is at a distance of the longitudinal axis 19 of the anchor screw and is delimited by a plane end face 18 that is oriented at a right angle to the cylinder barrel surface 17. Alternatively, the end face 18 can also deviate at a slight positive or negative angle, preferably not more than ±10°, from the right-angled orientation. All cutting edges are on a common plane and do not transverse the flanks 13. However, the cutting edges can also be on different planes.

REFERENCE NUMBERS LIST

1 Head
2 Outer octagon
3 Cross-shaped slot
4 Cap
5 Annular groove
6 Collar
7 Section
8 Shank
9 Section
10 Threaded part
11 Tip
12 Core
13 Flanks
14 Turn
15 Thread groove
16 Cutting edge
17 Cylinder barrel surface
18 End face
19 Longitudinal axis
20 Axis of 17

What is claimed is:

1. A self-drilling temporary screw implant for orthodontic treatment, said screw comprising:
   a self-drilling thread having a solid core;
   said thread being a single-flight, thread having flanks, spiraling about a core circumference toward a core tip, and thread grooves delimited by adjacent flanks; and
   a cutting edge disposed in at least one thread groove, said cutting edge being an edge of a recess formed in the at least one thread groove and extending both into and transverse to the adjacent flanks without traversing any of the adjacent flanks.

2. The screw implant according to claim 1, wherein the recess extends into a core of the screw implant.

3. The screw implant according to claim 1, wherein the cutting edge is on a plane.

4. The screw implant according to claim 3, wherein the plane of the cutting edge transverses a longitudinal axis of the screw implant at an angle within a range of −15° to +15°.

5. The screw implant according to claim 3, wherein the plane of the cutting edge transverses a longitudinal axis of the screw implant at an angle within a range of −10° to +10°.

6. The screw implant according to claim 1, wherein the plane of the cutting edge contains a longitudinal axis of the screw implant.

7. The screw implant according to claim 1, wherein the self-drilling thread has a self-grooving or self-cutting profile.

8. The screw implant according to claim 1, wherein a cross-section of the thread flanks, respectively, have an asymmetric profile.

9. The screw implant according to claim 1, wherein the cutting edge extends in a corresponding thread groove up to a height of not more than 70% of a depth of the thread groove, measured in a radial direction starting from a deepest point of cutting edge.

10. The screw implant according to claim 1, wherein every turn of the thread is provided with a corresponding cutting edge in the thread groove.

11. The screw implant according to claim 1, wherein several of the cutting edges are in a common plane.

12. The screw implant according to claim 1, wherein several cutting edges in several turns are regularly arranged around the core of the screw implant.

13. The screw implant according to claim 1, wherein the cutting edge in the thread groove delimits a recess that is part of a cylinder barrel surface whose axis extends transverse to a longitudinal axis of the screw implant and at a distance from same.

14. The screw implant according to claim 13, wherein the recess ends at a radial plane of the screw implant, the cutting edge being in that radial plane.

15. The screw implant according to claim 14, wherein at a distance from the core tip the thread has a constant core diameter D.

16. The screw implant according to claim 1, comprising a head having a diameter greater than an outside diameter of the thread.

17. The screw implant according to claim 16, wherein a thread-free cylindrical or conical shank is provided between the head and the thread.

18. The screw implant according to claim 1 wherein said recess is disposed in a shadow area of the cutting edge in order that bone material grown into the recess is not cut but only dislodged when the screw implant is screwed out of a bone.

* * * * *